US010729484B2

(12) United States Patent
Friedrichs et al.

(10) Patent No.: US 10,729,484 B2
(45) Date of Patent: Aug. 4, 2020

(54) ELECTROSURGICAL GENERATOR WITH CONTINUOUSLY AND ARBITRARILY VARIABLE CREST FACTOR

(71) Applicant: COVIDIEN LP, Mansfield, MA (US)

(72) Inventors: Daniel Friedrichs, Aurora, CO (US); James A. Gilbert, Boulder, CO (US); Steven C. Rupp, Arvada, CO (US)

(73) Assignee: Covidien LP, Mansfield, MA (US)

( * ) Notice: Subject to any disclaimer, the term of this patent is extended or adjusted under 35 U.S.C. 154(b) by 208 days.

(21) Appl. No.: 14/267,066

(22) Filed: May 1, 2014

(65) Prior Publication Data

US 2015/0025523 A1    Jan. 22, 2015

Related U.S. Application Data

(60) Provisional application No. 61/846,943, filed on Jul. 16, 2013.

(51) Int. Cl.
*A61B 18/12* (2006.01)
(52) U.S. Cl.
CPC .. *A61B 18/1206* (2013.01); *A61B 2018/1266* (2013.01)
(58) Field of Classification Search
CPC ............... A61B 18/1206; A61B 18/10; A61B 2018/1286; A61B 2018/1266
See application file for complete search history.

(56) References Cited

U.S. PATENT DOCUMENTS

| | | | |
|---|---|---|---|
| 3,252,052 A | 5/1966 | Nash | |
| 3,514,689 A | 5/1970 | Giannamore | |
| 3,551,786 A | 12/1970 | Van Gulik | |
| 3,641,422 A | 2/1972 | Farnsworth et al. | |
| 3,801,800 A | 4/1974 | Newton | |
| 3,885,569 A | 5/1975 | Judson | |
| 3,897,787 A | 8/1975 | Ikuno et al. | |
| 3,978,393 A | 8/1976 | Wisner et al. | |
| 4,102,341 A | 7/1978 | Ikuno et al. | |
| 4,287,557 A | 9/1981 | Brehse | |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

Kiprianoff M, Prime DC/AC Buck-Boost Converter: Derivation of mathematical models and evaluation of lumped transmission lines with focus on size and efficiency, Chalmers Bibliotek, 2012.*

(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

An electrosurgical generator is provided. The electrosurgical generator includes: a non-resonant radio frequency output stage configured to output a substantially square electrosurgical waveform; and a controller coupled to the non-resonant radio frequency output stage, the controller configured to adjust a crest factor of the substantially square electrosurgical waveform on a cycle-by-cycle basis.

20 Claims, 8 Drawing Sheets

(56) References Cited

U.S. PATENT DOCUMENTS

| | | |
|---|---|---|
| 4,378,801 A | 4/1983 | Oosten |
| 4,416,276 A | 11/1983 | Newton et al. |
| 4,416,277 A | 11/1983 | Newton et al. |
| 4,430,625 A | 2/1984 | Yokoyama |
| 4,436,091 A | 3/1984 | Banko |
| 4,438,766 A | 3/1984 | Bowers |
| 4,492,231 A | 1/1985 | Auth |
| 4,559,943 A | 12/1985 | Bowers |
| 4,569,345 A | 2/1986 | Manes |
| 4,572,190 A | 2/1986 | Azam et al. |
| 4,590,934 A | 5/1986 | Malis et al. |
| 4,630,218 A | 12/1986 | Hurley |
| 4,644,955 A | 2/1987 | Mioduski |
| 4,658,815 A | 4/1987 | Farin et al. |
| 4,658,820 A | 4/1987 | Klicek |
| 4,691,703 A | 9/1987 | Auth et al. |
| 4,739,759 A | 4/1988 | Rexroth et al. |
| 4,754,757 A | 7/1988 | Feucht |
| 4,767,999 A | 8/1988 | VerPlanck |
| 4,860,745 A | 8/1989 | Farin et al. |
| 4,887,199 A | 12/1989 | Whittle |
| 4,959,606 A | 9/1990 | Forge |
| 5,075,839 A | 12/1991 | Fisher et al. |
| 5,119,284 A | 6/1992 | Fisher et al. |
| 5,304,917 A | 4/1994 | Somerville |
| 5,318,563 A | 6/1994 | Malis et al. |
| 5,334,183 A | 8/1994 | Wuchinich |
| 5,370,672 A | 12/1994 | Fowler et al. |
| 5,372,596 A | 12/1994 | Klicek et al. |
| 5,396,194 A | 3/1995 | Williamson et al. |
| 5,438,302 A | 8/1995 | Goble |
| 5,472,443 A | 12/1995 | Cordis et al. |
| 5,500,616 A | 3/1996 | Ochi |
| 5,531,774 A | 7/1996 | Schulman et al. |
| 5,540,684 A | 7/1996 | Hassler, Jr. |
| 5,558,671 A | 9/1996 | Yates |
| 5,559,688 A | 9/1996 | Pringle |
| 5,596,466 A | 1/1997 | Ochi |
| 5,658,322 A | 8/1997 | Fleming |
| 5,674,217 A | 10/1997 | Wahlstrom et al. |
| 5,694,304 A | 12/1997 | Telefus et al. |
| 5,712,772 A | 1/1998 | Telefus et al. |
| 5,729,448 A | 3/1998 | Haynie et al. |
| 5,777,519 A | 7/1998 | Simopoulos |
| 5,792,138 A | 8/1998 | Shipp |
| 5,817,093 A | 10/1998 | Williamson, IV et al. |
| 5,871,481 A | 2/1999 | Kannenberg et al. |
| 5,936,446 A | 8/1999 | Lee |
| 6,017,354 A | 1/2000 | Culp et al. |
| 6,039,732 A | 3/2000 | Ichikawa et al. |
| 6,044,283 A | 3/2000 | Fein et al. |
| 6,059,781 A | 5/2000 | Yamanashi et al. |
| 6,063,075 A | 5/2000 | Mihori |
| 6,090,123 A | 7/2000 | Culp et al. |
| 6,142,992 A | 11/2000 | Cheng et al. |
| 6,162,217 A | 12/2000 | Kannenberg et al. |
| 6,222,356 B1 | 4/2001 | Taghizadeh-Kaschani |
| 6,235,020 B1 | 5/2001 | Cheng et al. |
| 6,243,654 B1 | 6/2001 | Johnson et al. |
| 6,261,286 B1 | 7/2001 | Goble et al. |
| 6,293,942 B1 | 9/2001 | Goble et al. |
| 6,296,636 B1 | 10/2001 | Cheng et al. |
| 6,306,134 B1 | 10/2001 | Goble et al. |
| 6,329,778 B1 | 12/2001 | Culp et al. |
| 6,364,877 B1 | 4/2002 | Goble et al. |
| 6,416,509 B1 | 7/2002 | Goble et al. |
| 6,426,886 B1 | 7/2002 | Goder |
| 6,629,974 B2 | 10/2003 | Penny et al. |
| 6,693,782 B1 | 2/2004 | Lash |
| 6,723,091 B2 | 4/2004 | Goble et al. |
| 6,740,079 B1 | 5/2004 | Eggers et al. |
| 6,819,027 B2 | 11/2004 | Saraf |
| 6,923,804 B2 | 8/2005 | Eggers et al. |
| 6,936,047 B2 | 8/2005 | Nasab et al. |
| 7,004,174 B2 | 2/2006 | Eggers et al. |
| 7,041,096 B2 | 5/2006 | Malis et al. |
| 7,244,255 B2 | 7/2007 | Daners et al. |
| 7,316,682 B2 | 1/2008 | Konesky |
| 7,324,357 B2 | 1/2008 | Miura et al. |
| 7,364,972 B2 | 4/2008 | Ono et al. |
| D574,323 S | 8/2008 | Waaler |
| 7,422,582 B2 | 9/2008 | Malackowski et al. |
| 7,511,472 B1 | 3/2009 | Xia et al. |
| 7,517,351 B2 | 4/2009 | Culp et al. |
| 7,722,603 B2 | 5/2010 | McPherson |
| 7,794,457 B2 | 9/2010 | McPherson et al. |
| 7,863,841 B2 | 1/2011 | Menegoli et al. |
| 8,100,898 B2 * | 1/2012 | Gregg ............... A61B 18/1233 606/32 |
| 8,231,614 B2 | 7/2012 | Dunning et al. |
| 8,257,349 B2 | 9/2012 | Orszulak |
| 8,608,733 B2 | 12/2013 | Orszulak |
| 9,585,709 B2 | 3/2017 | Krapohl |
| 2002/0029036 A1 | 3/2002 | Goble et al. |
| 2005/0004564 A1 * | 1/2005 | Wham ............... A61B 18/1206 606/34 |
| 2005/0197657 A1 * | 9/2005 | Goth ................... A61B 18/14 606/41 |
| 2009/0209956 A1 | 8/2009 | Marion |
| 2009/0248003 A1 | 10/2009 | Orszulak |
| 2009/0248007 A1 | 10/2009 | Falkenstein et al. |
| 2009/0254077 A1 | 10/2009 | Craig |
| 2010/0121318 A1 | 5/2010 | Hancock et al. |
| 2010/0174283 A1 * | 7/2010 | McNall, III ....... A61B 18/1485 606/45 |
| 2010/0268220 A1 | 10/2010 | Johnson et al. |
| 2011/0054460 A1 | 3/2011 | Gilbert |
| 2011/0071518 A1 | 3/2011 | Gilbert |
| 2011/0087213 A1 | 4/2011 | Messerly et al. |
| 2011/0115562 A1 | 5/2011 | Gilbert |
| 2011/0193608 A1 * | 8/2011 | Krapohl ............. A61B 18/1206 327/304 |
| 2011/0218526 A1 * | 9/2011 | Mathur ............. A61B 18/1206 606/33 |
| 2011/0319881 A1 | 12/2011 | Johnston |
| 2012/0215216 A1 * | 8/2012 | Friedrichs ......... A61B 18/1206 606/38 |
| 2013/0035679 A1 | 2/2013 | Orszulak |
| 2013/0041364 A1 | 2/2013 | Orszulak |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079673 A1 | 3/2013 | Stein et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |
| 2014/0025064 A1 | 1/2014 | Collins |
| 2014/0163431 A1 | 6/2014 | Orszulak et al. |
| 2014/0171935 A1 | 6/2014 | Digmann et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |

(56) References Cited

FOREIGN PATENT DOCUMENTS

| | | | |
|---|---|---|---|
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 694291 A1 | 1/1996 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1151725 A1 | 11/2001 |
| EP | 1157667 A2 | 11/2001 |
| EP | 1366724 A1 | 12/2003 |
| EP | 1500378 A1 | 1/2005 |
| EP | 1681026 A2 | 7/2006 |
| EP | 1776929 A1 | 4/2007 |
| EP | 1849425 A1 | 10/2007 |
| EP | 2100566 A1 | 9/2009 |
| EP | 2353533 A2 | 8/2011 |
| EP | 2469699 A2 | 6/2012 |
| EP | 2777577 A1 | 9/2014 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 702510 | 1/1954 |
| GB | 1290304 A | 9/1972 |
| GB | 2132893 A | 7/1984 |
| GB | 2434872 A | 8/2007 |
| JP | 63 005876 A | 1/1988 |
| JP | 2002-065690 A | 3/2002 |
| JP | 2005-185657 A | 7/2005 |
| JP | 2011161230 A | 8/2011 |
| JP | 2012135203 A | 7/2012 |
| SU | 166452 | 11/1964 |
| SU | 727201 A1 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 2008/043999 A2 | 4/2008 |
| WO | 20080044000 A1 | 4/2008 |
| WO | 08/053532 A1 | 5/2008 |
| WO | 2008135736 A1 | 11/2008 |

OTHER PUBLICATIONS

Tucker J, Understanding output voltage limitations of DC/DC buck converters, 2008, Analog Applicantions Journal, pp. 11-13.*
European Search Report No. 14177244.2 dated Feb. 3, 2015.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Extended European Search Report from Application No. EP 14158040.7 dated May 26, 2014.
Extended European Search Report from Application No. EP 14156761.0 dated Jul. 7, 2014.
Wald et al., "Accidental Burns", JAMA, Aug. 16, 1971, vol. 217, No. 7, pp. 916-921.
Vallfors et al., "Automatically Controlled Bipolar Electrosoagulation— 'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. Mi, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.

(56) References Cited

OTHER PUBLICATIONS

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
Chinese Office Action dated Sep. 4, 2017 for application No. 20140302980.0 with English Translation.
Australian Examination Report dated May 3, 2018 issued in Australian Appln. No. 2014202749.
Japanese Office Action for application No. 2014-128168 dated May 10, 2018 with English Translation (20 pages).
Chinese Office Action for Application No. 201410302980.0 dated Apr. 18, 2018 with English translation (15 pages).
Japanese Office Action dated Oct. 23, 2018 issued in corresponding JP Application No. 2014-128168.
Chinese Office Action dated Oct. 8, 2018 issued in corresponding CN Application No. 201410302980.0.
Chinese Rejection Decision dated Apr. 28, 2019 issued in corresponding CN Appln. No. 201410302980.0.
Japanese Notice of Allowance dated Mar. 29, 2019 issued in corresponding JP Appln. No. 2014-128168. (Summary only).
The European Examination Report dated Jul. 12, 2019 issued in corresponding EP Appln. No. 14 177 244.2.

\* cited by examiner

ELECTROSURGICAL GENERATOR WITH CONTINUOUSLY AND ARBITRARILY VARIABLE CREST FACTOR

CROSS-REFERENCE TO RELATED APPLICATION

The present application claims the benefit of and priority to U.S. Provisional Patent Application No. 61/846,943, filed Jul. 16, 2013, the entire contents of which are incorporated by reference herein.

BACKGROUND

1. Technical Field

The present disclosure relates to an electrosurgical system and method for operating an electrosurgical generator. More particularly, the present disclosure relates to a system, method and apparatus for adjusting crest factor of electrosurgical waveforms generated by an electrosurgical generator having a DC-DC buck converter and a DC-AC boost converter.

2. Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. A forceps is a pliers-like instrument which relies on mechanical action between its jaws to grasp, clamp and constrict vessels or tissue. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue. However, the above example is for illustrative purposes only and there are many other known bipolar electrosurgical instruments which are within the scope of the present disclosure.

Electrosurgical procedures outlined above may utilize various tissue and energy parameters in a feedback-based control system. There is continual need to improve delivery of energy to the tissue.

SUMMARY

According to one embodiment, the present disclosure provides for an electrosurgical generator. The electrosurgical generator includes: a non-resonant radio frequency output stage configured to output a substantially square electrosurgical waveform; and a controller coupled to the non-resonant radio frequency output stage, the controller configured to adjust a crest factor of the substantially square electrosurgical waveform on a cycle-by-cycle basis.

According to one aspect of the above embodiment, the non-resonant radio frequency output stage further includes: a DC-DC buck converter configured to output a DC waveform, the DC-DC buck converter including at least one first switching element operated at a first duty cycle.

According to one aspect of the above embodiment, the non-resonant radio frequency output stage further includes: a DC-AC boost converter coupled to the DC-DC buck converter and including at least one second switching element operated at a second duty cycle, the DC-AC boost converter configured to convert the DC waveform to generate the substantially square electrosurgical waveform.

According to one aspect of the above embodiment, the controller is coupled to the DC-DC buck converter and the DC-AC boost converter and the controller is further configured to adjust the first duty cycle and the second duty cycle to adjust the duty cycle of the substantially square electrosurgical waveform.

According to one aspect of the above embodiment, the first duty cycle adjusts a peak voltage of each cycle of the substantially square electrosurgical waveform.

According to one aspect of the above embodiment, the second duty cycle adjusts a duty cycle of the substantially square electrosurgical waveform.

According to one aspect of the above embodiment, generator includes a user input for selecting a desired crest factor and the controller is configured to adjust the first and second duty cycles in response to the desired crest factor.

According to another embodiment, the present disclosure provides for an electrosurgical generator. The electrosurgical generator includes: a DC-DC buck converter configured to output a DC waveform, the DC-DC buck converter including at least one first switching element operated at a first duty cycle; a DC-AC boost converter coupled to the DC-DC buck converter and including at least one second switching element operated at a second duty cycle, the DC-AC boost converter configured to convert the DC waveform to generate a substantially square electrosurgical waveform; and a controller coupled to the DC-DC buck converter and the DC-AC boost converter and configured to adjust the first duty cycle and the second duty cycle to adjust a crest factor of the substantially square electrosurgical waveform on a cycle-by-cycle basis.

According to one aspect of the above embodiment, the first duty cycle adjusts a voltage of each cycle of the substantially square electrosurgical waveform.

According to one aspect of the above embodiment, wherein the second duty cycle adjusts a duty cycle of the substantially square electrosurgical waveform.

According to one aspect of the above embodiment, the generator includes a user input for selecting a desired crest factor and the controller is configured to adjust the first and second duty cycles in response to the desired crest factor.

According to a further embodiment, the present disclosure provides for method for controlling an electrosurgical generator. The method includes: operating at least one first switching element of a DC-DC buck converter at a first duty cycle to output a DC waveform; operating at least one second switching element of a DC-AC boost converter coupled to the DC-DC buck converter at a second duty cycle to convert the DC waveform to generate a substantially square electrosurgical waveform; and adjusting the first duty cycle and the second duty cycle to operate the at least one electrosurgical waveform to adjust a crest factor of the substantially square electrosurgical waveform on a cycle-by-cycle basis.

According to one aspect of the above embodiment, the method further includes: controlling the first duty cycle to adjust a peak voltage of each cycle of the substantially square electrosurgical waveform.

According to one aspect of the above embodiment, the method further includes: controlling the second duty cycle to adjust a duty cycle of the substantially square electrosurgical waveform.

According to one aspect of the above embodiment, the method further includes: selecting a desired crest factor; and adjusting the first and second duty cycles in response to the desired crest factor.

According to one aspect of the above embodiment, the method further includes: measuring at least one of a tissue or energy property; and adjusting the first and second duty cycles in response to the measured tissue or energy property.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
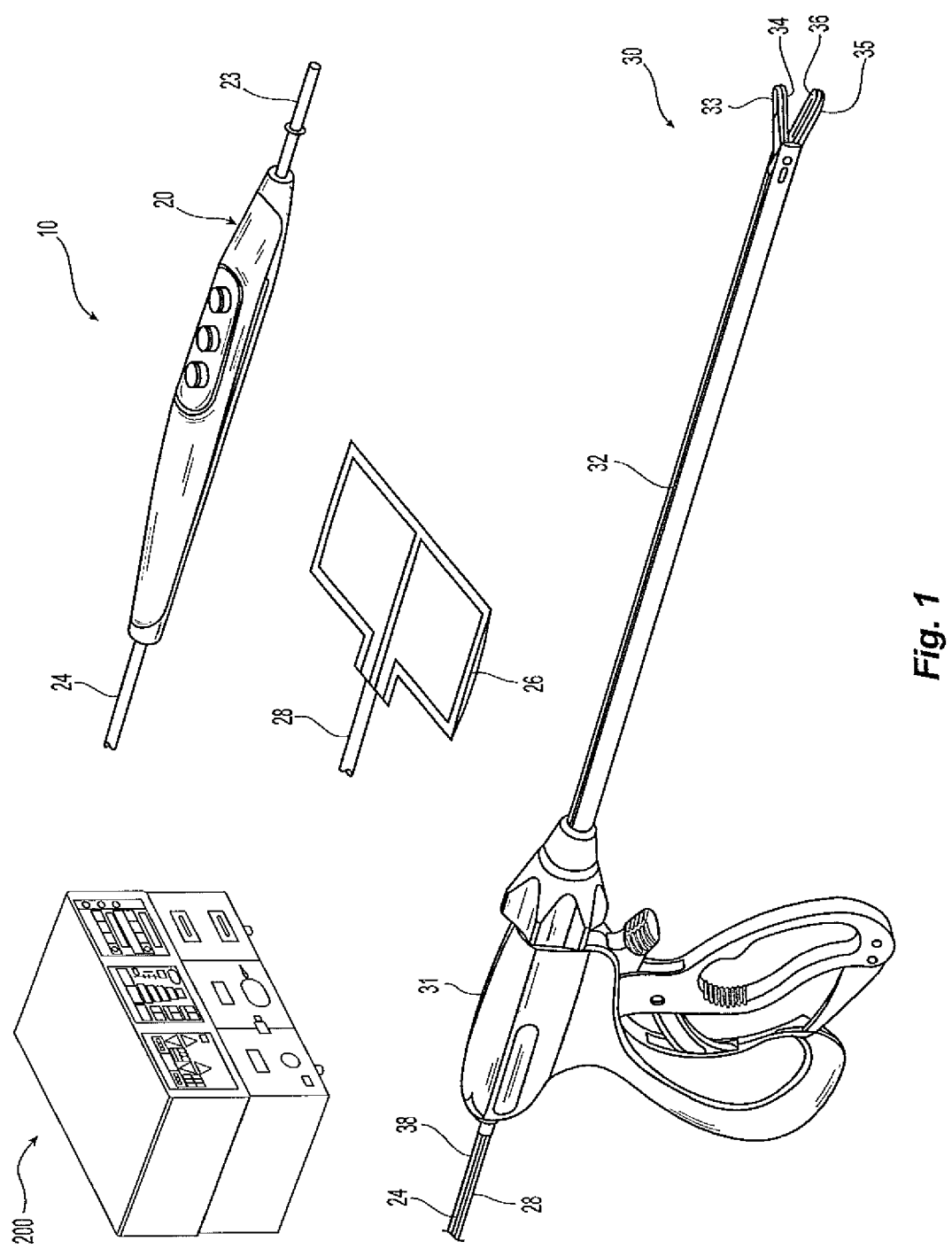
FIG. 1 is a perspective view of the components of one illustrative embodiment of an electrosurgical system according to the present disclosure.

FIG. 1 is a perspective view of the components of one illustrative embodiment of a bipolar and monopolar electrosurgical system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating current is supplied to the instrument 20 by a generator 200 via a supply line 24 that is connected to an active terminal 230 (FIG. 3) of the generator 200, allowing the instrument 20 to cut, coagulate, ablate and/or otherwise treat tissue. The alternating current is returned to the generator 200 through a return electrode pad 26 via a return line 28 at a return terminal 32 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
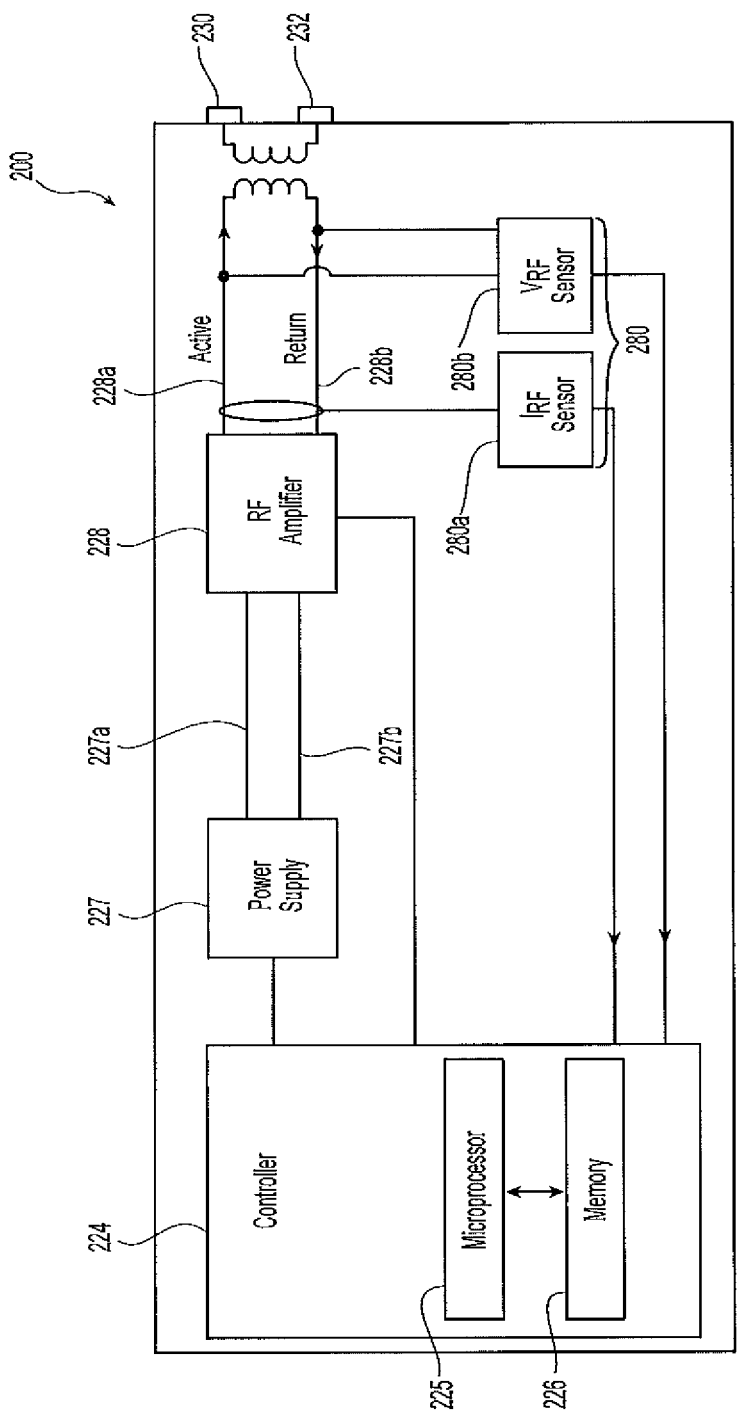
FIG. 3 is a schematic, block diagram of the embodiment of an electrosurgical generator of FIG. 2 according to the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28 coupled to the active and return terminals 230, 232, respectively (FIG. 3). The electrosurgical forceps 30 is coupled to the generator 200 at a connector having connections to the active and return terminals 230 and 232 (e.g., pins) via a plug disposed at the end of the cable 38, wherein the plug includes contacts from the supply and return lines 24, 28 as described in more detail below.

Figure 2:
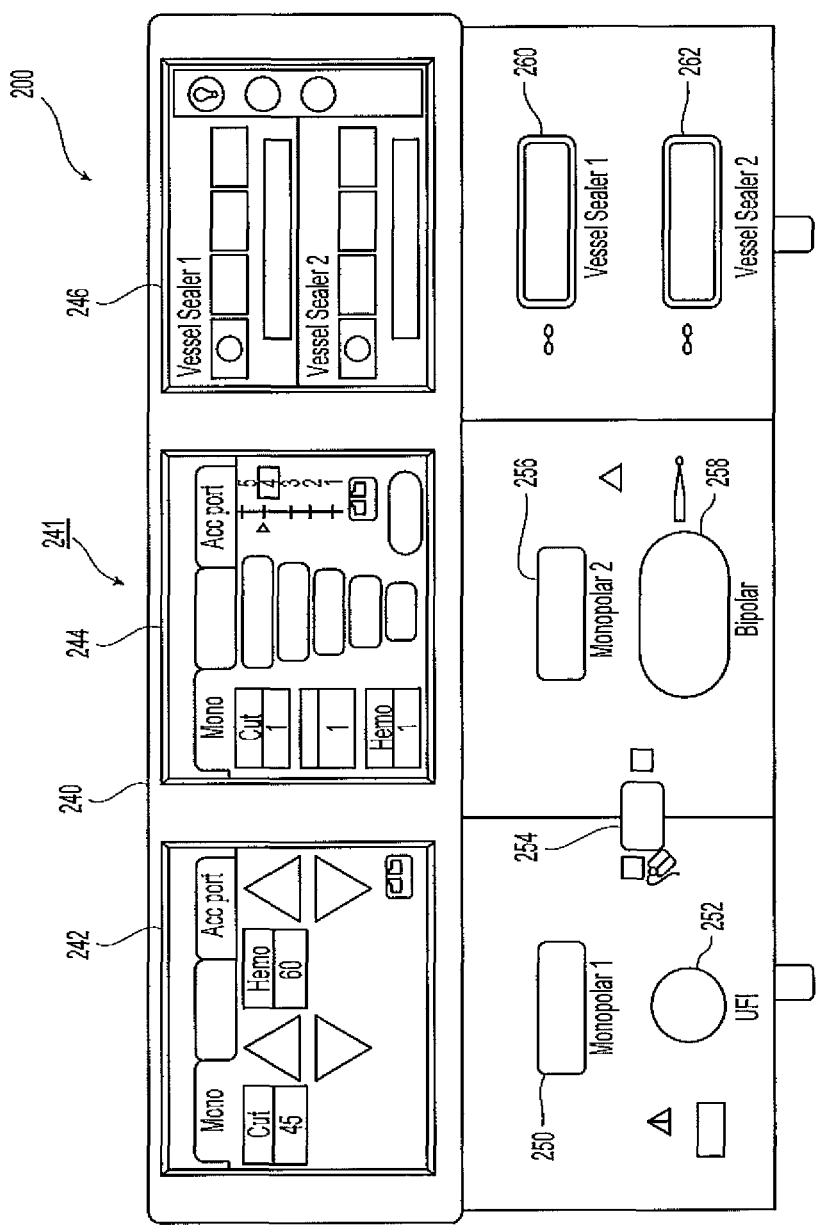
FIG. 2 is a front view of one embodiment of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 30, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 30, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 20) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 30 that may be plugged into the connectors 260 and 262. The generator 200 outputs energy through the connectors 260 and 262 suitable for sealing tissue grasped by the forceps 30. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each forceps 30 being utilized, such that various instruments provide the user with a specific intensity scale corresponding to the forceps 30.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The energy is returned thereto via the return terminal 232. The active and return terminals 230 and 232 and coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively.

Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RE voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 20 and/or forceps 30. The controller 224 utilizes the input signals to adjust power outputted by the generator 200 and/or performs other control functions thereon.

Figure 4:
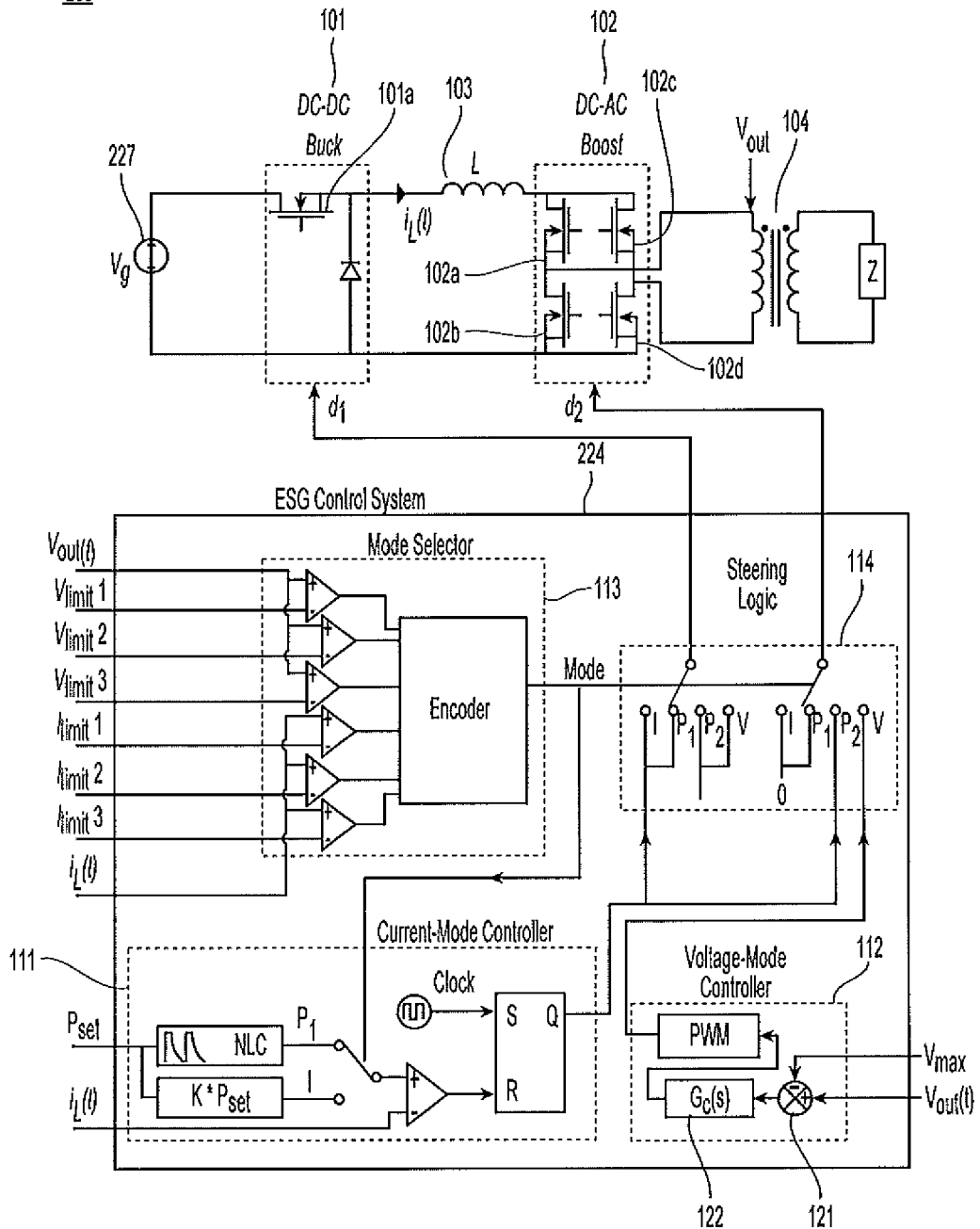
FIG. 4 is a schematic, block diagram of a DC-DC converter and a DC-AC inverter of the electrosurgical generator of FIG. 2 according to the present disclosure.

FIG. 4 shows another embodiment of the generator 200 configured to operate with near-deadbeat control to maintain a desired AC output of generator 200. As used herein, the terms "deadbeat" or "near-deadbeat" refer to adjustments being made by the generator 200 to the output from about 1 cycle of the waveform to about 100 cycles, in embodiments from about 10 cycles to about 25 cycles. The term cycle refers to a full cycle of an electrosurgical alternating waveform having a positive and negative half cycle. The generator 200 according to the present disclosure may have an operating frequency of from about 100 kHz to about 1,000 kHz, and in certain embodiments, from about 200 kHz to about 500 kHz, thus the generator 200 operating at the predetermined frequency of 100 kHz outputs a waveform having 100,000 cycles per second.

The adjustments to the output can be made at the same frequency (e.g., 1 cycle of the electrosurgical waveform) or a factor of about 0.1 (e.g., every 10 cycles of the electrosurgical waveform). In accordance with an exemplary embodiment, near-deadbeat control minimizes unintentional charring by ensuring that only a desired quantum of power is delivered to the electrosurgical instrument. In the prior art generators, slow transient response of the converter to changes in load impedance may result in excessive delivery of power that may not be detected for 500 cycles or more.

The generator 200 is also configured to operate in any of a constant voltage limit mode, a constant current limit mode, a constant power mode, and combinations thereof. The mode selection is generally based on the impedance associated with the tissue being cut. Different types of tissue, such as muscle and fat, have different impedances. In terms of electrosurgical operations, constant power output tends to uniformly vaporize tissue, resulting in clean dissection. Whereas constant voltage output tends to explosively vaporize or carbonize tissue ("black coagulation"), and constant current output tends to thermally coagulate tissue without vaporization ("white coagulation"). Carbonization is surgically useful if the surgeon wishes to rapidly destroy surface tissue, and thermal coagulation is regularly coupled with mechanical pressure to seal hepatic or lymphatic vessels shut. However, the surgeon generally desires to operate using constant power output and importantly, return to using constant power output as quickly as possible if there is deviation.

Figure 5:
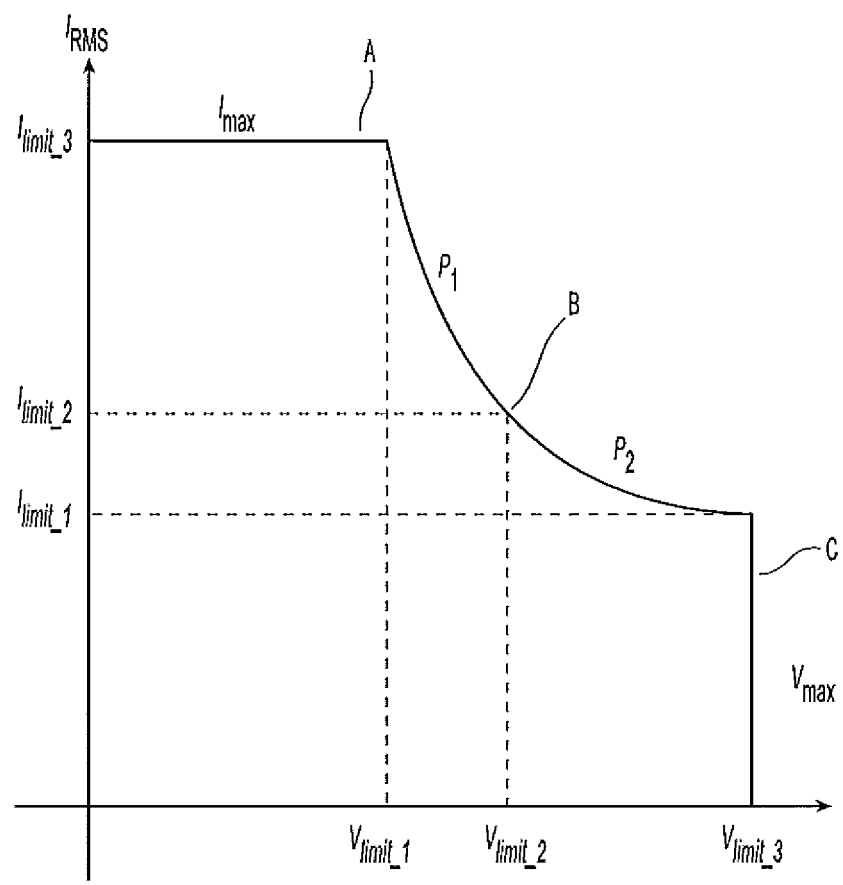
FIG. 5 is a graphical representation of desired output characteristics according to the present disclosure.

With respect to the AC output of the generator 200 and in exemplary embodiments, "constant power" is defined to mean the average power delivered in each switching cycle is substantially constant. Likewise, "constant voltage" and "constant current" are defined as modes where the root mean square (RMS) value of the AC voltage or current, respectively, is regulated to a substantially fixed value. An exemplary graphical representation of the desired output characteristics is illustrated in FIG. 5. In an exemplary embodiment, as the load impedance increases and voltage increases, the corresponding increasing output voltage triggers a transition from a constant current mode shown as region A to a constant power mode shown as region B and to a constant voltage mode shown as region C. Similarly, in an exemplary embodiment, as the load impedance decreases and current increases, the corresponding decreasing output voltage triggers the opposite transition from the constant voltage region C to the constant power region B and to the constant current region A.

With reference to the schematic shown in FIG. 4, the generator 200 includes a DC-DC buck converter 101, a DC-AC boost converter 102, an inductor 103, a transformer 104, and the controller 224. In embodiments, the DC-DC buck converter 101 and the DC-AC boost converter 102 are part of the RF output stage 228. In the exemplary embodiment, a DC voltage source Vg, such as the power supply 227, is connected to DC-DC buck converter 101. Furthermore, inductor 103 is electrically coupled between DC-DC buck converter 101 and DC-AC boost converter 102. The output of DC-AC boost converter 102 transmits power to the primary winding of transformer 104, which passes through the secondary winding of transformer 104 to the load Z (e.g., tissue being treated).

The DC-DC buck converter 101 includes a switching element 101a and the DC-AC boost converter 102 includes a plurality of switching elements 102a-102d arranged in an H-bridge topology. In embodiments, the DC-AC boost converter 102 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In an exemplary embodiment, controller 224 is in communication with both DC-DC buck converter 101 and DC-AC boost converter 102, in particular, the switching elements 101a and 102a-102d, respectively. The controller 224 is configured to output control signals, which may be a pulse-width modulated signal, to the switching elements 101a and 102a-102d as described in further detail below with respect to the voltage-mode controller 112. In particular, the controller 224 is configured to control the duty cycle d1 of the control signal supplied to the switching element 101a of the DC-DC buck converter 101 and the duty cycle d2 of the control signals supplied to the switching elements 102a-102d of the DC-AC boost converter 102. Additionally, controller 224 is configured to measure power characteristics of generator 200, and control generator 200 based at least in part on the measured power characteristics. Examples of the measured power characteristics include the current through inductor 103 and the voltage at the output of DC-AC boost converter 102. In an exemplary embodiment, controller 224 controls buck converter 101 by generating the duty cycle d1 based on a comparison of the inductor current and a nonlinear carrier control current for every cycle.

In accordance with an exemplary embodiment, controller 224 includes a current-mode controller 111, a voltage-mode controller 112, a mode selector 113, and steering logic 114. The mode selector 113 compares the output voltage $V_{out}(t)$ and the inductor current $i_L(t)$ to set limits in order to determine the desired mode of operation of the generator 200. The operational mode may be of constant (or maximum) current $I_{max}$ (e.g., constant current region A), constant power $P_1$ from DC-DC buck converter 101, constant power $P_2$ from DC-AC boost converter 102 (e.g., constant power region B), or constant (or maximum) voltage $V_{max}$ (e.g., constant voltage region C) as illustrated in FIG. 5, or combinations thereof. The output selection of mode selector 113 is communicated to steering logic 114. In an exemplary embodiment, steering logic 114 controls which of at least one of current-mode controller 111 and voltage mode controller 112 are enabled. Furthermore, steering logic 114 selects which conversion stage receives the output of current-mode controller 111 and/or voltage-mode controller 112.

In one exemplary embodiment, steering logic 114 switches between operating either DC-DC buck converter 101 or DC-AC boost converter 102 with current-mode control for constant power, depending on which portion of the desired output characteristics is being produced. The voltage mode controller 112 and/or current mode controller 111 adjust the duty cycles d1 and/or d2 for current mode control. Furthermore, steering logic 114 selects the duty cycle that each of DC-DC buck converter 101 and/or DC-AC boost converter 102 receives.

The current-mode controller 111 compares the inductor current $i_L(t)$ to nonlinear carrier control current $i_C(t)$ (e.g., desired set point current). In an exemplary embodiment, the nonlinear carrier control current $i_C$ is set by the selection of Pset (e.g., desired power set point), which may be done by a user, or provided by a lookup table. In an exemplary embodiment, current-mode controller 111 uses a latch circuit to compare inductor current $i_L(t)$ to either a current limit signal (I) or a power limit signal ($P_l$). The control signal for the latch circuit is the mode signal, which is communicated from steering logic 114. The inputs of the latch circuit are a clock signal and either the current limit signal (I) or a power limit signal ($P_l$). The selection of the current-mode controller 111 output is in response to the current mode of the generator 200. The operating mode of the generator 200 may be communicated by the mode selector 113. In an exemplary embodiment, the switching waveform d(t) is switched "high" at the start of a switching period if the inductor current $i_L(t)$ is lower than nonlinear carrier control current $i_C(t)$. Furthermore, in the exemplary embodiment, the switching waveform d(t) is switched "low" in response to the inductor current $i_L(t)$ exceeding the nonlinear carrier control current $i_C(t)$. In other words, a comparison of the inductor current $i_L(t)$ to nonlinear carrier control current $i_C(t)$ facilitates adjusting pulse duration of duty cycle d1 of the buck converter 101, as previously described.

To generate and control a constant current from generator 200, the average value of inductor current $i_L(t)$ is set to be substantially equal to fixed control current limit K*Pset. For small inductor current ripple, in other words $\Delta i_L \ll I_L$, the current-mode controller regulates the inductor current $i_L(t)$ to an approximately constant value, which is substantially equal to the fixed control current limit. In accordance with an exemplary embodiment, the current-mode controller 111 is able to maintain an approximately constant value of inductor current $i_L(t)$ by adjusting the current within from about 1 cycle to about 100 cycles, in embodiments from about 2 to about 20 cycles, in further embodiments, from about 3 to about 10 cycles. This low cycle adjustment provides for near-deadbeat or deadbeat control as described above.

In an exemplary embodiment and with continued reference to FIG. 4, voltage-mode controller 112 of the controller 224 includes a comparator 121, a compensator 122, and a pulse-width modulator (PWM) 123. In an exemplary embodiment, voltage-mode controller 112 compares the output voltage $V_{out}(t)$ with a reference voltage $V_{max}$ at comparator 121. The output of comparator 121 is communicated to compensator 122, which in turn, outputs an error signal that drives PWM 123. In the exemplary embodiment, the output of compensator 122 is passed through PWM 123, which sets the duty cycle d2 of the signal in certain modes.

Furthermore, in an exemplary embodiment, mode selector 113 includes an encoder and performs multiple comparisons. With respect to FIG. 5, the mode selector 113 uses the voltage comparison signals and the current comparison signals to determine whether generator 200 is operating in the constant current output region (A), the region P1 of the constant power output region (B), the region P2 of the constant power output region (B), or the constant voltage output region (C). Furthermore, the output mode signal from mode selector 113 controls the switch position in steering logic 114. When output voltage $V_{out}(t)$ exceeds the first voltage limit $V_{limit\_1}$, the second voltage limit $V_{limit\_2}$, and the third voltage limit $V_{limit\_3}$, then the encoder selects the constant voltage mode. The constant voltage mode signal from mode selector 113 causes the position of the switches of steering logic 114 to a "V" position as illustrated in FIG. 4 and Table 1 below, which shows duty cycle of DC-DC buck converter 101 and DC-AC boost converter 102 by operating mode. In table 1, the values "1" may be set to any fixed duty cycle below 100%.

TABLE 1

| | $I_{max}$ | P1 | P2 | $V_{max}$ |
|---|---|---|---|---|
| Buck Converter | Current-programmed mode (CPM) controlled with fixed control current limit | CPM controlled with non-linear carrier control limit | 1 | 1 |
| Boost Converter | 1 | 1 | CPM controlled with fixed control current limit | Voltage mode controlled |

In various alternative embodiments, the selection of operating modes is based in part on the duty cycle. For example, if the generator 200 is operating in constant power mode using the DC-DC buck converter 101 and the duty cycle reaches 100% active, the controller 224 may be configured to switch to the constant power region A using the DC-AC boost converter 102. The switch to the boost converter enables the generator 200 to operate over a higher range of impedances.

With respect to constant power output mode, constant AC power output is achieved by setting one or both of duty cycle d1 and duty cycle d2 to desired values. Moreover, generator 200 operates with constant AC power output in either a first constant power region P1 or a second constant power region P2. In various embodiments, the converter switches of the steering logic 114 between generating constant power using DC-DC buck converter 101 or DC-AC boost converter 102, depending on the impedance of the load. Moreover, in various embodiments, generator 200 may operate both DC-DC buck converter 101 and/or DC-AC boost converter 102 at the same time, which results in a constant power output having a high voltage and low power.

In steady-state and operating in first constant power region P1, inductor current $i_L(t)$ is compared to a nonlinear carrier control current $i_C(t)$ in current-mode controller 111. The pulse duration of the duty cycle d1 of the DC-DC buck converter is varied using the current mode controller 111. The varying pulse duration of the duty cycle controls the inductor current $i_L(t)$, which is responsive to the load in contact with the buck converter. As the impedance of the load varies, the voltage across and the current through the inductor 103 also vary. As previously described, at the beginning of the duty cycle, the active portion of the duty cycle is initiated. In response to the inductor feedback signal exceeding the nonlinear carrier control current, the duty cycle switches to the non-active portion. The duty cycle stays in the non-active portion until the end of the duty cycle, upon which the next duty cycle begins in the active portion. In alternative embodiments, during the comparison of the inductor feedback signal and the nonlinear carrier control current, once the control current exceeds the inductor current, the duty cycle switches to the active portion. In accordance with the exemplary embodiment, generator 200 generates constant power using DC-DC buck converter 101.

In steady-state and operating in second constant power region P2, the average voltage of $V_i(t)$ is constant in response to the input voltage Vg being constant, the DC-DC buck converter 101 is also disabled, since there is no voltage across inductor 103. The use of current programmed mode control results in the average current of $i_L(t)$ being regulated to an approximately fixed value with deadbeat or near-deadbeat control. In order to regulate $i_L(t)$, duty cycle d2 is varied by the current mode controller to maintain $i_L(t)$ at a fixed value. Given the fixed voltage and current, the power at input of DC-AC boost converter 102 is also constant. In an exemplary embodiment, the DC-AC boost converter 102 is nearly lossless, resulting in the output power being approximately equal to the input power. Since the input power is constant, the output power of DC-AC boost converter 102 is also constant.

With respect to constant voltage output mode, constant voltage output is achieved by setting duty cycle d1 of DC-DC buck converter 101 to a fixed value, and duty cycle d2 of DC-AC boost converter 102 is voltage-mode controlled. In an exemplary embodiment, the voltage-mode control involves measuring the output voltage of DC-AC boost converter 102 with a sensor network, feeding the sensed output voltage to a control loop in voltage-mode controller 112, and adjusting the converter's duty cycle command based on the relative difference between the measured output voltage and the reference output voltage. In other words, the duty cycle d2 is set to increase or decrease the output voltage to match $Y_{limit}$. In an exemplary embodiment, $V_{limit}$ may be set by a user or based on values in a look-up table. In an alternative embodiment, the boost inverter is run at a fixed duty cycle with no feedback of the output voltage.

With respect to constant current output mode, constant current output is achieved by operating DC-AC boost converter 102 at a fixed duty cycle d2 and current-mode controlling DC-DC buck converter 101. In an exemplary embodiment, the current-mode control accurately controls the average inductor current such that the output of buck converter 101 is a constant current. In one constant current embodiment, current-mode controller 111 compares inductor current $i_L(t)$ to a constant current $i_C$, which is set by K*Pset, where K*Pset is a constant current set by the user during use. In various embodiments, Pset is set during the design stage.

In other words, controller 224 is configured to vary duty cycle d1 in order to maintain inductor current $i_L(t)$ at the fixed value. As a result, the constant current output mode produces an AC output current whose magnitude is regulated with near-deadbeat speed. In an exemplary embodiment, the generator 200 implementing the three modes of constant power, constant voltage, or constant current produces a very fast, very accurate regulation of the AC output characteristic. Various modes are impacted by monitored characteristics, while other modes do not need to respond to the same monitored characteristics. Specifically, controller 224 may switch between operating modes based in part on monitored characteristics, such as inductor current and voltage. In other words, the selection of which stage of the converter to current-mode control is achieved with minimal feedback and without a need for extraneous measurements, averaging, or feedback of the output. Also, and as previously mentioned, the controller 224 performs near deadbeat control by regulating inductor current to an approximately constant value, equal to a reference current.

Transitioning between the three modes, in an exemplary embodiment, is determined by monitoring the voltage of the primary winding of transformer 104 and the inductor current. Furthermore, the determination of transitioning between the modes is also based on the voltage and current of inductor 103. The controller 224 transitions modes from constant current to constant power to constant voltage as the output voltage increases. Specifically, in an exemplary embodiment, the generator 200 operates in the constant current mode if the output voltage is less than a first voltage limit ($V_{limit\_1}$). If the output voltage exceeds the first voltage limit, the generator 200 transitions to a first constant power mode (P1). If the output voltage exceeds a second voltage limit ($V_{limit\_2}$), the generator 200 transitions to a second constant power mode (P2). If the output voltage exceeds a third voltage limit ($V_{limit\_3}$), the generator 200 transitions to the constant voltage mode, where the output voltage is limited and held constant. In an exemplary embodiment, the first voltage limit ($V_{limit\_1}$), the second voltage limit ($V_{limit\_2}$), and the third voltage limit ($V_{limit\_3}$) are set by a user or by the generator 200 (e.g., from a look-up table).

Similarly, an exemplary controller 224 transitions from constant voltage mode to constant power mode and to constant current mode as inductor current $i_L(t)$ increases. Specifically, in an exemplary embodiment, the generator 200 operates in the constant voltage mode if the inductor current does not exceed a first current limit ($I_{limit\_1}$). If the inductor current does exceed the first current limit ($I_{limit\_1}$), then the mode transitions to the second constant power mode (P2). If the inductor current exceeds a second current limit ($I_{limit\_2}$), then the mode transitions to the first constant power mode (P1). If the inductor current exceeds a third current limit ($I_{limit\_3}$), the generator 200 transitions to the constant current mode, where the inductor current is limited and held constant. In an exemplary embodiment, the first current limit ($I_{limit\_1}$), the second current limit ($I_{limit\_2}$), and the third current limit ($I_{limit\_3}$) are set by a user or by the generator (e.g., from a look-up table).

As described above, in order to achieve the constant current region A, the DC-DC buck converter 101 is controlled in current-program mode (CPM) and the DC-AC boost converter 102 is fixed at about 100% duty cycle d2. In order to achieve the constant power region B, in one embodiment the DC-DC buck converter 101 is controlled in non-linear carrier control (NLC) mode and the DC-AC boost converter 102 is fixed at about 100% duty cycle d2. In another embodiment, the DC-DC buck converter 101 is fixed at about 100% duty cycle d1 and the DC-AC boost converter 102 is controlled in CPM. In order to achieve the constant voltage region B, the DC-DC buck converter 101 is fixed at 100% duty cycle d1 and the DC-AC boost converter 102 is fixed at a predetermined duty cycle d2, which may be less than 100%.

Figure 6:
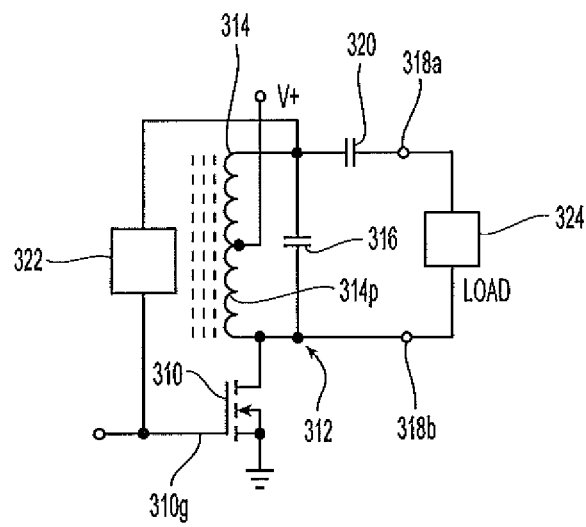
FIG. 6 is a schematic, block diagram of a prior art electrosurgical generator having a resonant circuit.
Figure 7:
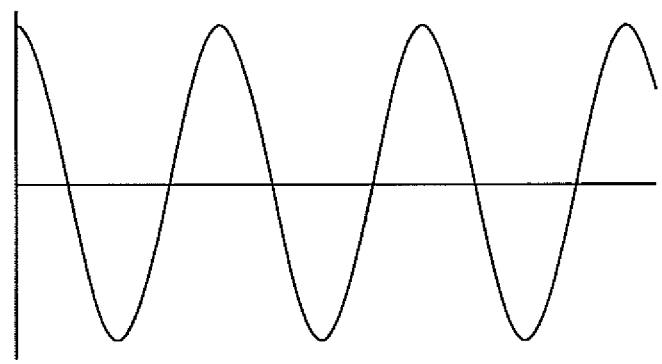
FIG. 7 is a graphical representation of a prior art sinusoidal electrosurgical waveform.
Figure 8:
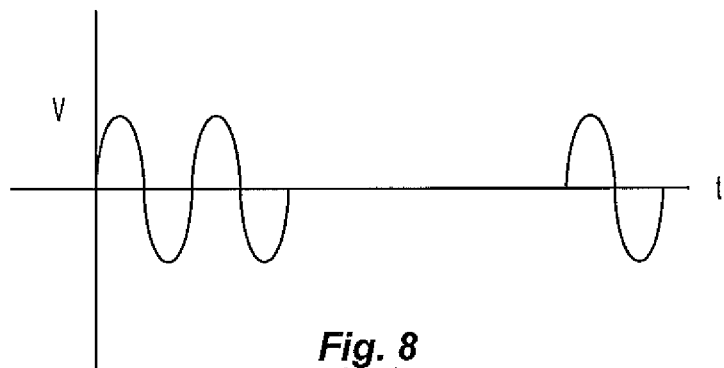
FIG. 8 is a graphical representation of a prior art sinusoidal electrosurgical waveform having a modulated duty cycle.

With reference to FIGS. 6-8, certain conventional electrosurgical include resonant networks that generate sinusoidal waveforms as disclosed in U.S. Pat. No. 5,438,302, the entire contents of which are incorporated by references herein.

With reference to FIG. 6, a prior art electrosurgical generator 300 includes an oscillator with a MOSFET oscillator device 310 coupled in series with a resonant output network 312 between a positive voltage supply rail V+ and a ground. The resonant network 312 has an inductor configured as an autotransformer 314 with a parallel tuning capacitance 316 coupled across the complete winding and a pair of output terminals 318a, 318b, which are connected to an electrosurgical load 324 (e.g., tissue) as shown in FIG. 7. The terminal 318a is isolated from the transformer 314 and parallel capacitor 316 by a series coupling capacitor 320. One portion of the transformer secondary winding acts as a primary winding 314p which is coupled between the supply V+ and the drain terminal of the MOSFET 310. A feedback circuit 322 links one end of the secondary winding to a gate terminal 310g of the MOSFET 310. The generator 300 also includes a capacitor that provides a feedback voltage to the gate terminal 310g. Voltage applied to the gate terminal 310g of the MOSFET 310 drives the MOSFET 310 between the fully "on" and fully "off" states, such that the resonant network 312 generates a sinusoidal waveform across the secondary winding. The voltage supplied to the MOSFET 310 may be modulated to generate waveforms having a variable crest factor.

As used herein, the term "crest factor" denotes a ratio of peak voltage to RMS voltage. Crest factor is directly related to the tissue effects applied to tissue. Higher crest factors result in long, high-energy arcs applied to the tissue, which increase coagulation effects. Low crest factor result in lower energy arcs useful in increasing cutting effects. Voltage applied to the gate terminal 310g is of fixed carrier frequency that is modulated to achieve a desired crest factor setting. Thus, a fixed carrier frequency is modulated at a second, modulation frequency, to achieve a waveform having a desired duty cycle/crest factor.

The fixed carrier frequency may be from about 100 kHz to about 1,000 kHz, and in certain embodiments, from about 200 kHz to about 500 kHz. The modulating frequency may be from about 5 kHz to about 50 kHz, in certain embodiments from about 10 kHz to about 40 kHz. In particular, a duty cycle of the fixed carrier frequency signal is adjusted to obtain a desired crest factor, since varying the duty cycle varies the RMS, which in turn affects the crest factor. With reference to FIG. 8, the modulation of the fixed carrier signal is illustrated, which shows a modulated waveform having higher crest factor waveforms by lowering the duty cycle (e.g., two cycles ON, three cycles OFF).

There are a number of drawbacks with this approach. The relatively low frequency of the modulating frequency is capable of stimulating muscle tissue. Thus, paralytic anesthesia is required to prevent this effect, although "muscle capture," e.g., stimulation of muscle by the electrosurgical generator is often still present. In addition, modulating a fixed carrier signal produces harmonics, which require significant design and manufacturing modifications associated with electrical noise suppression, filtering, interference with other systems (e.g., return electrode monitoring etc.). Further, conventional generators only include a discrete number of fixed crest factor settings associated with preset electrosurgical modes having "optimal" settings that provide desired tissue effects. However, a discrete number of fixed crest factor settings limits available tissue effects and requires that "optimal" settings be programmed into the generator.

The generator 200 according to the present disclosure is capable of outputting electrosurgical waveforms having any user-settable crest factor, such that the waveforms have an infinitely variable crest factor which may be adjusted on a cycle-by-cycle basis. In embodiments, the duty cycle may be adjusted manually, e.g., by the user, or automatically, e.g., by the generator 200, in response to energy delivery feedback or any other suitable parameter, e.g., time, as described in further detail below.

Figure 10:
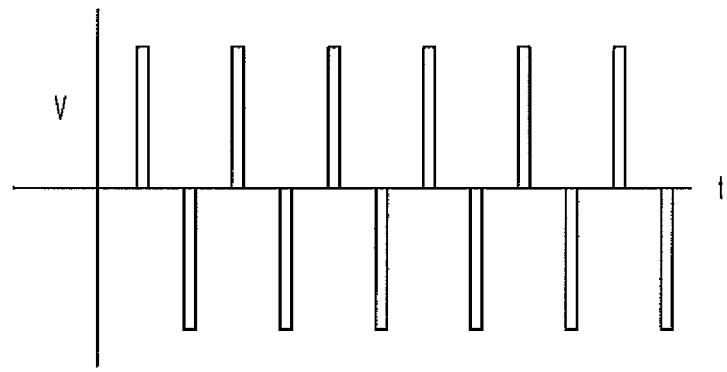
FIG. 10 is a graphical representation of a square electrosurgical waveform having a uniform crest factor output by the electrosurgical generator of FIG. 2 according to the present disclosure.
Figure 11:
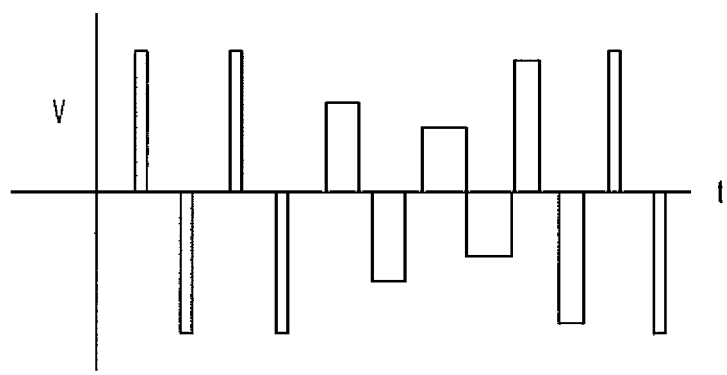
FIG. 11 is a graphical representation of a square electrosurgical waveform having a varying crest factor output by the electrosurgical generator of FIG. 2 according to the present disclosure.

As discussed above, the generator 200 includes the DC-AC boost converter 102 that is directly coupled to the transformer 104, which is in turn coupled directly to the patient via electrosurgical instrument 20 and/or forceps 30. The generator 200 does not include any resonant circuit coupled between the boost converter 102 and the transformer 104, which allows for generation of square electrosurgical waveforms as shown in FIGS. 9-11.

Figure 9:
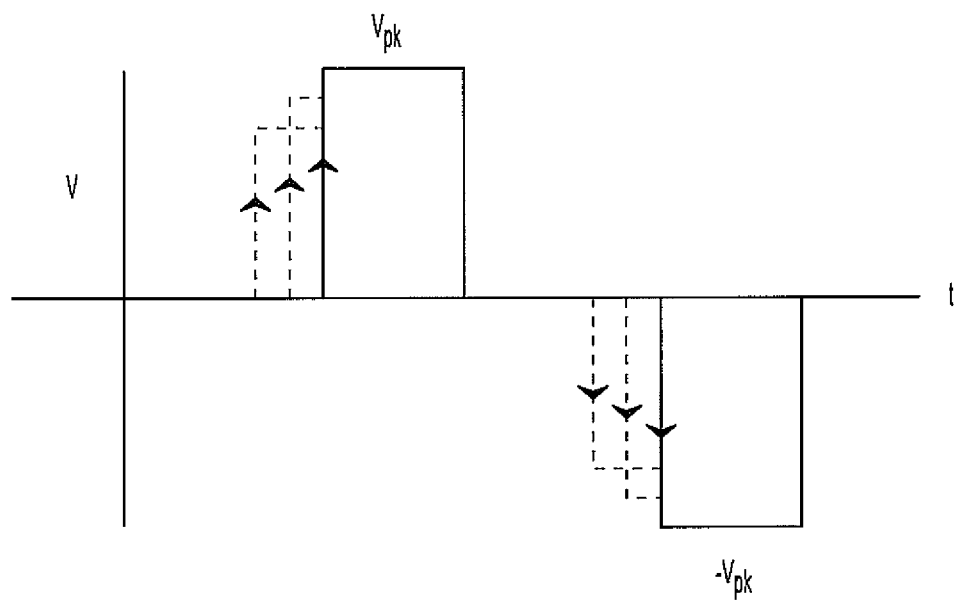
FIG. 9 is a graphical representation of a square electrosurgical waveform output by the electrosurgical generator of FIG. 2 according to the present disclosure.

With reference to FIG. 9, the generator 200 is configured to generate a waveform having a plurality of cycles with varying cycle lengths (e.g., duty cycle) and peak voltages, while maintaining the root mean square voltage, thus the power being supplied is unchanged. Variations in the peak voltage of each of the cycles also vary the crest factor for each of the cycles, allowing for cycle-by-cycle crest factor adjustments. Adjustments to the peak voltage are accomplished by the DC-DC buck converter 101, namely, by adjusting the duty cycle d1 of the control signal supplied to the switching element 101a of the DC-DC buck converter 101. Adjustments to the length of the RF cycles are accomplished at the DC-AC boost converter 102.

In particular, the controller 224 adjusts the duty cycle d2 of the control signals supplied to the switching elements 102a-102d of the DC-AC boost converter 102.

Since the duty cycle and the peak voltage of the cycles of the resulting waveforms can be varied to any arbitrary interval, the crest factor of the waveform can be varied to any arbitrary value as well. Thus, waveforms with any desirable crest factor can be produced with the value of the crest factor being continuously adjustable, such as those shown in FIGS. 10 and 11.

In embodiments, the generator 200 may include discrete crest factor settings, which may be input via the user interface 241. With reference to FIG. 10, a non-modulated electrosurgical waveform having a discrete crest factor is shown. In further embodiments, the generator 200 may include an input for continuously varying the crest factor. The user interface 241 may include a setting to adjust the crest factor. In further embodiments, electrosurgical instrument 20 and/or forceps 30 or other input devices (e.g., foot switch) may include inputs to adjust the crest factor. In additional embodiments, the crest factor may be adjusted by the controller 224 automatically based on changes in energy and/or tissue properties (e.g., impedance). In particular, the generator 200 may measure any suitable energy and/or tissue parameter using the sensors 280 including, but not limited to, voltage, current, phase, impedance, arc luminosity, arc length, temperature, force exerted on the instrument, and combinations thereof and automatically adjust the crest factor in response to this measurement. FIG. 11, shows an electrosurgical waveform having varying cycle width, thereby changing the crest factor, while maintaining the same power due to the change in peak voltage based on varying crest factor input.

Using continuous, rather than modulated, waveforms to achieve higher crest factors allows for reduction in muscle stimulation generated during electrosurgical energy. Additionally, design and manufacturing challenges associated with filtering and electrical noise generated through the modulation process are significantly reduced. Finally, the ability to arbitrarily and continuously adjust the crest factor of an electrosurgical waveform presents the opportunity to achieve novel new tissue effects, improve surgeon control, and achieve the desired tissue result.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   a non-resonant radio frequency output stage configured to output a substantially square electrosurgical waveform, the substantially square electrosurgical waveform having a plurality of cycles repeating at an operating frequency, each of the cycles including a positive half cycle and a negative half cycle;
   a sensor configured to measure a feedback parameter; and
   a controller coupled to the non-resonant radio frequency output stage, the controller configured to adjust a crest factor of the substantially square electrosurgical waveform at an adjustment frequency, which is the same as the operating frequency of the electrosurgical waveform, according to the measured feedback parameter.

2. The electrosurgical generator according to claim 1, wherein the non-resonant radio frequency output stage further comprises:
   a DC-DC buck converter configured to output a DC waveform, the DC-DC buck converter including at least one first switching element operated at a first duty cycle.

3. The electrosurgical generator according to claim 2, wherein the non-resonant radio frequency output stage further comprises:
   a DC-AC boost converter coupled to the DC-DC buck converter and including at least one second switching element operated at a second duty cycle, the DC-AC boost converter configured to convert the DC waveform to generate the substantially square electrosurgical waveform.

4. The electrosurgical generator according to claim 3, wherein the controller is coupled to the DC-DC buck converter and the DC-AC boost converter, and the controller is further configured to adjust the first duty cycle and the second duty cycle to adjust a duty cycle of the substantially square electrosurgical waveform.

5. The electrosurgical generator according to claim 4, wherein the controller is configured to adjust, as part of the first duty cycle, a peak voltage of each cycle of the substantially square electrosurgical waveform.

6. The electrosurgical generator according to claim 5, wherein the controller is configured to adjust, as part of the second duty cycle, the duty cycle of the substantially square electrosurgical waveform.

7. The electrosurgical generator according to claim 6, further comprising a user input for selecting a desired crest factor, and the controller is configured to adjust the first and second duty cycles in response to the desired crest factor.

8. The electrosurgical generator according to claim 1, wherein the feedback parameter is tissue impedance.

9. The electrosurgical generator according to claim 1, wherein the feedback parameter includes one or more of output power, output current, or output voltage.

10. An electrosurgical generator, comprising:
a DC-DC buck converter configured to output a DC waveform, the DC-DC buck converter including at least one first switching element operated at a first duty cycle;
a DC-AC boost converter coupled to the DC-DC buck converter and including at least one second switching element operated at a second duty cycle, the DC-AC boost converter configured to convert the DC waveform to generate a substantially square electrosurgical waveform, the substantially square electrosurgical waveform having a plurality of cycles repeating at an operating frequency, each of the cycles including a positive half cycle and a negative half cycle;
a sensor configured to measure a feedback parameter; and
a controller coupled to the DC-DC buck converter and the DC-AC boost converter and configured to adjust the first duty cycle and the second duty cycle to adjust a crest factor of the substantially square electrosurgical waveform at an adjustment frequency, which is the same as the operating frequency of the electrosurgical waveform, according to the measured feedback parameter.

11. The electrosurgical generator according to claim 10, wherein the controller is configured to adjust, as part of the first duty cycle, a voltage of each cycle of the substantially square electrosurgical waveform.

12. The electrosurgical generator according to claim 11, wherein the controller is configured to adjust, as part of the second duty cycle, a duty cycle of the substantially square electrosurgical waveform.

13. The electrosurgical generator according to claim 12, further comprising a user input for selecting a desired crest factor, and the controller is configured to adjust the first and second duty cycles in response to the desired crest factor.

14. The electrosurgical generator according to claim 10, wherein the measured feedback parameter is tissue impedance.

15. A method for controlling an electrosurgical generator, the method comprising:
operating at least one first switching element of a DC-DC buck converter at a first duty cycle to output a DC waveform;
operating at least one second switching element of a DC-AC boost converter coupled to the DC-DC buck converter at a second duty cycle to convert the DC waveform to generate a substantially square electrosurgical waveform, the substantially square electrosurgical waveform having a plurality of cycles repeating at an operating frequency, each of the cycles including a positive half cycle and a negative half cycle; and
adjusting the first duty cycle and the second duty cycle to operate the electrosurgical generator to adjust a crest factor of the substantially square electrosurgical waveform at an adjustment frequency, which is the same as the operating frequency of the electrosurgical waveform, according to a measured feedback parameter.

16. The method according to claim 15, further comprising:
controlling the first duty cycle to adjust a peak voltage of each cycle of the substantially square electrosurgical waveform.

17. The method according to claim 15, further comprising:
controlling the second duty cycle to adjust a duty cycle of the substantially square electrosurgical waveform.

18. The method according to claim 15, further comprising:
selecting a desired crest factor; and
adjusting the first and second duty cycles in response to the desired crest factor.

19. The method according to claim 15, further comprising:
measuring at least one of a tissue or energy property; and
adjusting the first and second duty cycles in response to the measured tissue or energy property.

20. The method according to claim 15, wherein the measured feedback parameter is tissue impedance.

* * * * *